(12) United States Patent
Subba Rao et al.

(10) Patent No.: US 6,336,941 B1
(45) Date of Patent: Jan. 8, 2002

(54) MODULAR HIP IMPLANT WITH SHOCK ABSORPTION SYSTEM

(76) Inventors: G. V. Subba Rao, 806 E. Mary La.; Anil K. Goli, 153 E. Halt Dr., both of Terre Haute, IN (US) 47802

(*) Notice: Subject to any disclaimer, the term of this patent is extended or adjusted under 35 U.S.C. 154(b) by 0 days.

(21) Appl. No.: 09/474,282

(22) Filed: Dec. 29, 1999

Related U.S. Application Data

(63) Continuation-in-part of application No. 09/134,632, filed on Aug. 14, 1998, now abandoned.

(51) Int. Cl.⁷ ............................... A61F 2/32; A61F 2/36
(52) U.S. Cl. .................. 623/22.42; 623/23.17
(58) Field of Search ............ 623/22.42, 22.43, 623/22.44, 22.45, 22.46, 23.17, 23.15, 23.21, 23.22

(56) References Cited

U.S. PATENT DOCUMENTS

| | | | |
|---|---|---|---|
| 3,987,499 A | 10/1976 | Scharbach et al. | |
| 4,051,559 A | 10/1977 | Pifferi | |
| 4,938,773 A | 7/1990 | Strand | |
| 5,258,033 A | 11/1993 | Lawes et al. | |
| 5,362,311 A | * 11/1994 | Amino et al. | 623/22 |
| 5,389,107 A | 2/1995 | Nassar et al. | |
| 5,507,830 A | 4/1996 | DeMane et al. | |

FOREIGN PATENT DOCUMENTS

| | | |
|---|---|---|
| DE | 25 24 923 | 5/1975 |
| FR | 2 701 206 | 9/1993 |
| SU | 171 8883 A1 | 3/1990 |
| SU | 1718883 | * 3/1992 ............... 623/23.17 |

OTHER PUBLICATIONS

Smith+Nephew, "Thompson Hip Endoprosthesis System," Thompson Stems, p. B–8.
Smith+Newphew, "Moore Hip Endoprosthesis System Solid and Fenestrated Stems.," p. B–6.
Howmedica, "Partnership, Ad," Partnership System, , p. 1.
Smith+Newphew, "Richards Modular Hip System," Femoral Components, , p. A–12.
Smith+Newphew, "Richards Modular Hip System," Femoral Components, contd., , p. A–13.
Plus Endoprothetik, CS– and CSL–PLUS Cemented–Hip–System.
Arthroplasty of Hip, "Text," p. Total: 9.

* cited by examiner

*Primary Examiner*—David H. Willse
*Assistant Examiner*—Alvin Stewart

(57) ABSTRACT

A modular hip implant that can be custom fit to an individual patient, including a shock absorption system that absorbs compressive stresses that are imparted to the implant. The size of the femoral ball member, size of the femoral stem, femoral neck length, and tension in the shock absorption system are all individually adjustable parameters, depending on the particular patient. A unique coupling member houses a modular spring mechanism that serves as the shock absorber. The coupling member is received into the ball member to an adjustable depth, the adjustment of which varies the length of the femoral neck. The length of the femoral neck can be adjusted during surgery without requiring additional parts.

10 Claims, 6 Drawing Sheets

MODULAR HIP IMPLANT WITH SHOCK ABSORPTION SYSTEM

CROSS REFERENCE TO RELATED U.S. APPLICATION

This application is a continuation-in-part of U.S. Application Ser. No. 09/134,632, filed Aug. 14, 1998 now abandoned.

BACKGROUND OF THE INVENTION

The present invention relates in general to an orthopaedic hip implant, and in particular to a modular orthopaedic hip implant that can be custom fit to a patient. The present invention also relates to an implant having a shock absorption system which increases patient comfort and the life of the implant.

Prosthetic implants for the replacement of a portion of a patient's hip joints are well-known, and are typically available as a two to three component system. The femoral stem component includes a shank at its distal end which extends into the medullary canal of the femur and is fixed therein using bone cement or other means known in the art. At the proximal end of the femoral stem is a neck which typically terminates in a spherical ball that is adapted to cooperate with the patient's acetabulum or a prosthetic acetabular cup fixed into the patient's acetabulum. The ball, neck and femoral stem are typically formed in one piece from cobalt-chromium-molybdenum, titanium or other suitable material. The acetabular cup is typically formed as a metal hemispherical bowl and, optionally, can be provided with a plastic insert that is fixed therein to enhance the sliding engagement between the ball and the acetabular cup.

Conventional one-piece femoral component designs are available in different sizes, but they do not allow enough flexibility for variations in individual parameters of the patient's anatomy. Parameters such as femoral neck length, femoral shank length and diameter, and femoral head size can vary independently of one another. For example, the length of the femoral neck can vary independently of the size of the femoral head or length of the medullary canal. It can thus be difficult to find a suitably fitting implant when selecting the implant from the different sizes available as one-piece femoral components.

To address this problem, modular implant systems are known. For example, U.S. Pat. No. 4,938,773 to Strand discloses a femoral stem which can be fitted with interchangeable, different size femoral neck portions. Such a system is undesirably limited by the availability of different size components. Further, a large quantity of different size components must be produced and stocked to ensure that all patients can be fitted.

Similarly, U.S. Pat. No. 5,507,830 to DeMane discloses a modular hip prosthesis which includes a plurality of removable, different size tubular sleeves that can be attached to a cylindrically shaped stem of the femoral component, thereby allowing the surgeon to extend the stem length as necessary. Also disclosed are interchangeable sleeves that can be added to the neck portion of the implant to elongate the neck portion of the prosthesis. Removable pads are provided for attachment to the mid-section of the prosthesis for changing the cross-sectional configuration thereof. Again, such a system is limited by the availability of different size sleeves or extensions.

Another problem with conventional hip implants is that countless compressive stresses are transmitted thereto from daily activities such as walking, running, exercising, sitting and standing. These compressive stresses can eventually cause painful fractures and can often result in the implant loosening after several years. Ultimately, revision surgery may become necessary.

Prosthetic hip implants that address impact problems are known in the art. For example, SU 1718883-A1 discloses a modular implant that includes a spring disposed at the end face of the femoral neck, the threaded end of which is screwed into the base of the femoral component. The spring is rigidly mounted in the bottom of a recess formed in the prosthetic femoral head and provides shock absorption for the implant.

U.S. Pat. No. 5,389,107 to Nassar et al. discloses a prosthetic hip implant having an elongate element that extends coaxially from the ball section of the femur component. The elongate element slidably extends into a chamber formed by a tubular insert that is secured in the femur. Contained at the bottom of the chamber is a spring against which the elongate element abuts, thereby providing shock absorption. A pin member extends from the bottom of the chamber and slidably fits into a bore formed in the elongate element. A second spring is disposed between the pin and the bottom of the bore to provide further shock absorption.

What is needed is an improved modular implant that also provides shock absorption.

SUMMARY OF THE INVENTION

The present invention provides a modular hip implant that can be custom fit to an individual patient and that includes a shock absorption system that absorbs compressive stresses that are imparted to the implant.

In one form thereof, the present invention provides a modular hip prosthesis. The hip prosthesis comprises a ball member having an outer surface adapted to cooperate with an acetabular socket and a femoral stem having a shank adapted to be inserted and secured into a medullary cavity of a femur. The femoral stem has a neck at a proximal end thereof which is connected to the ball member. A spring mechanism is disposed intermediate the ball member and the neck, and provides cushioning movement between the femoral stem and the ball member. The spring mechanism is detachably connected to the neck and detachably connected to the ball member.

In a preferred form, the modular hip prosthesis further comprises a bore disposed in the ball member. A coupling member houses the spring mechanism, and the connection of the ball member to the spring mechanism is through the coupling member. The coupling member is received in the bore to an adjustable depth, adjustment of which causes corresponding adjustment of the distance the neck extends from the ball member. More preferably, the bore and the coupling member comprise corresponding threads, the coupling member being threadingly received in the bore. Still more preferably, the spring mechanism includes a first connector at a first end thereof connecting the neck to the spring mechanism. The first connector and the neck include complementary threads, such that the first connector is threadingly connected to the neck. The spring mechanism includes a second connector at a second end thereof connecting the spring mechanism to the coupling member.

In another form thereof, the present invention provides a method of custom fitting a hip prosthesis to an individual patient. In this method, a ball member is selected from a plurality of different size ball members, depending upon the size of the acetabular socket into which the ball member is to be inserted. A femoral component is selected from a plurality of different size femoral components, and the neck of the selected femoral component is attached to a coupling member. A depth that the coupling member is to be inserted into the selected ball member is determined. Such depth corresponds to an individual patient. The coupling member is installed into the ball member to the determined depth.

In a preferred form of the inventive method, a spring mechanism is installed in the prosthesis to allow cushioning movement of the neck of the selected femoral component relative to the ball member. More preferably, the spring mechanism is selected from a plurality of spring mechanisms having spring elements of different spring constants or stiffnesses. The spring stiffness can be calibrated to the weight of the patient. Further, the length of the neck can be adjusted intraoperatively to compensate for errors in neck length obtained from preoperative imaging techniques.

One advantage of the present invention is that the spring mechanism absorbs much of the compressive stresses imparted to the implant during daily activities such as walking, running and exercising. Because the spring mechanism contracts and expands to absorb load bearing, shock and compressive stresses imparted to the hip joint during weight bearing and mobilization, the implant is less likely to loosen, and the useful life of the implant is therefore lengthened. The spring mechanism also reduces other complications, such as dislocation of the femoral stem from the acetabulumn, acetabular damage and erosion, and protrusion of the femoral ball member into the acetabulum and pelvis during a sudden jarring event, such as a fall.

Another advantage of the present invention is that the spring mechanism is a modular component such that a spring element having a specific stiffness can be selected.

Another advantage of the present invention is that the length of the femoral neck can be changed without adding or interchanging parts, unlike the above-described prior art implants which require a plurality of interchangeable parts. Instead, the present invention employs a single coupling member that can be installed in the ball member to a depth which corresponds to the desired length of the femoral neck.

Yet another advantage of the present invention is that the length of the femoral neck can be adjusted intraoperatively. While pre-operative imaging techniques can be used to determine the appropriate length of the femoral neck, such techniques are often only an approximation of actual surgical conditions. With the present invention, adjustments to the length of the femoral neck can be made during surgery by adjusting the depth to which the coupling member is inserted into the ball member so that an exact preoperative neck length need not be entirely relied upon.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Figure 1:
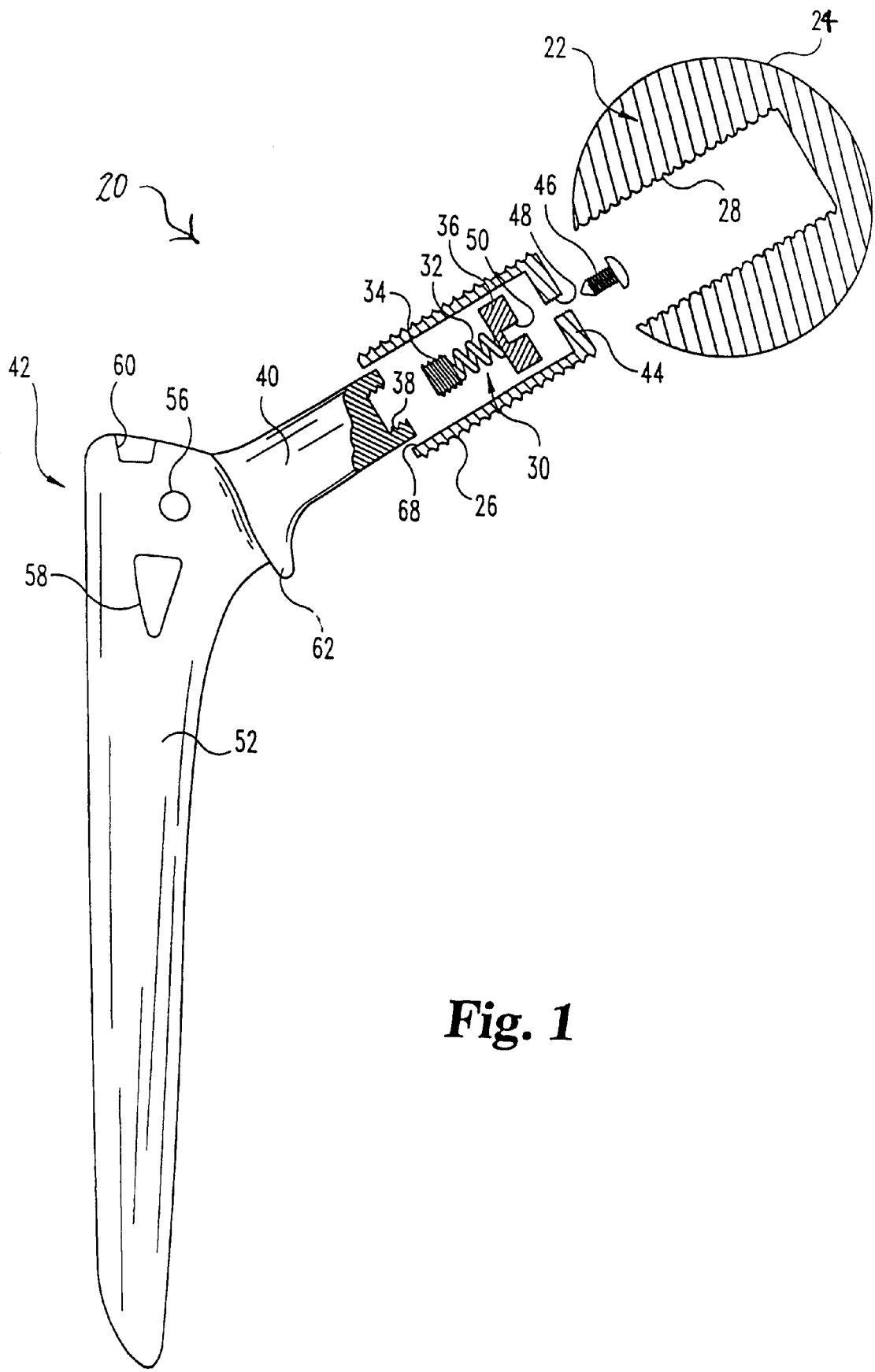
FIG. 1 is an exploded side sectional view of a modular hip implant incorporating the present invention.

Corresponding reference characters indicate corresponding parts throughout the several views. The exemplification set forth herein illustrates preferred embodiments of the invention, in several forms, and such exemplifications are not to be construed as limiting the scope of the invention in any manner.

DETAILED DESCRIPTION

Figure 2:
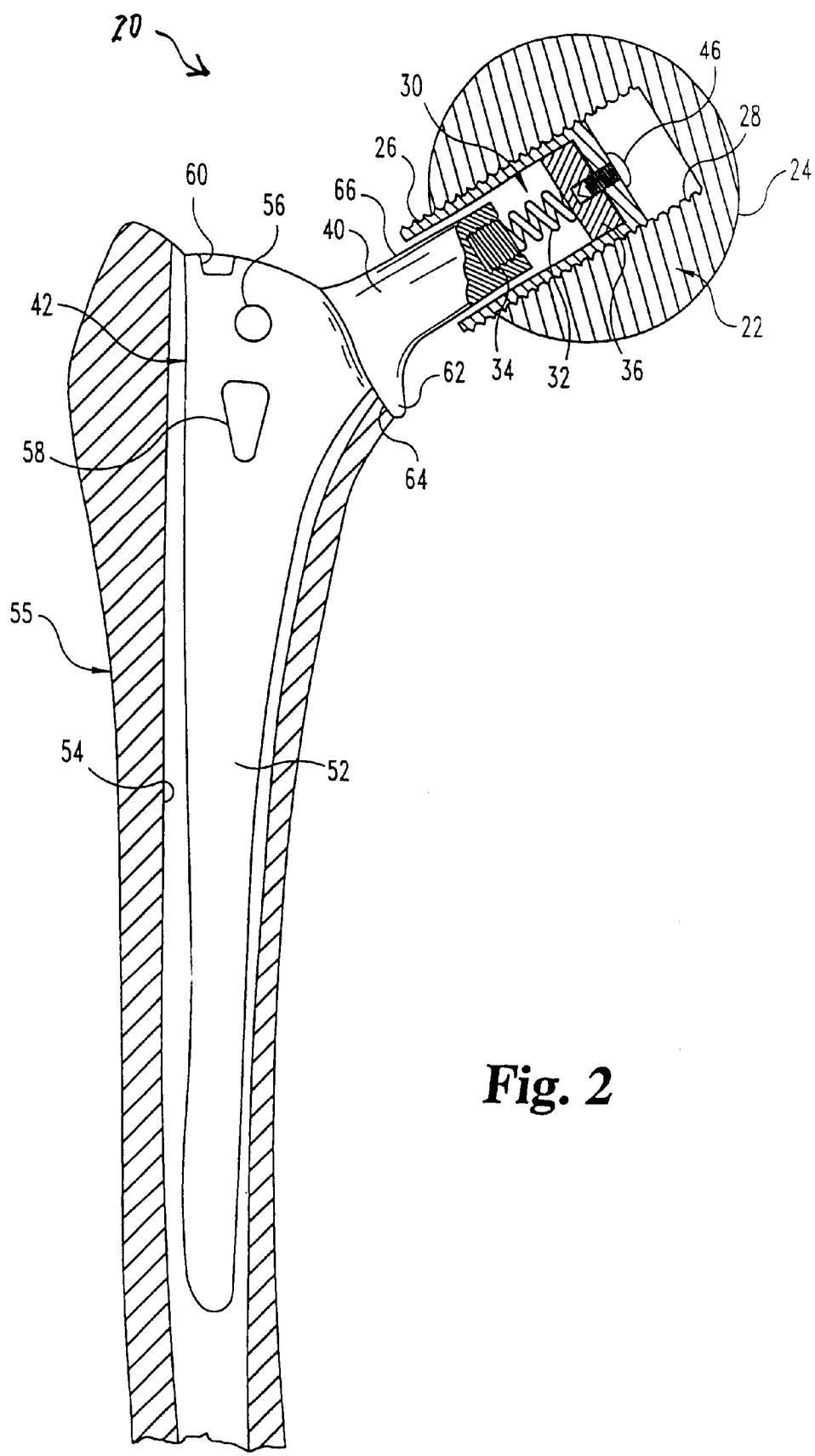
FIG. 2 is side sectional view of the modular hip implant of FIG. 1.
Figure 3A:
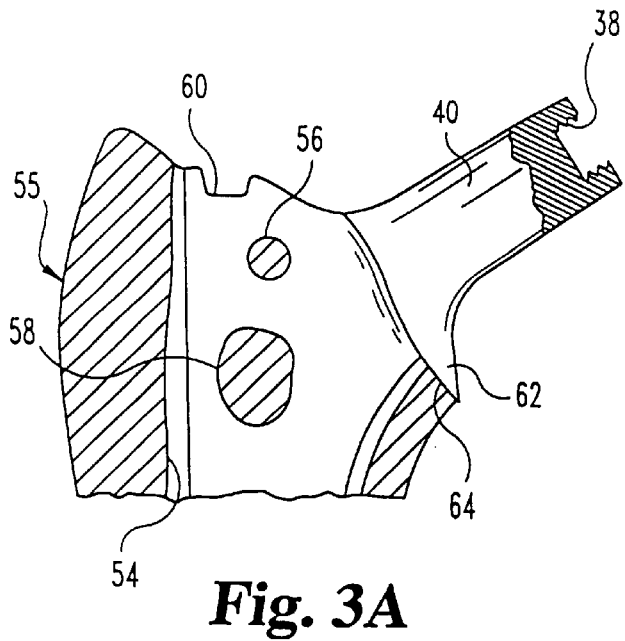
FIG. 3A is a fragmentary sectional view illustrating the femoral neck of a femoral stem component.
Figure 3B:
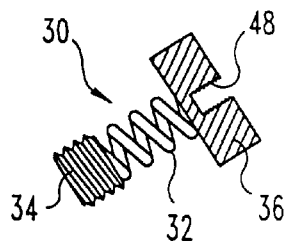
FIG. 3B is a sectional view illustrating a spring mechanism incorporating the present invention.
Figure 3C:
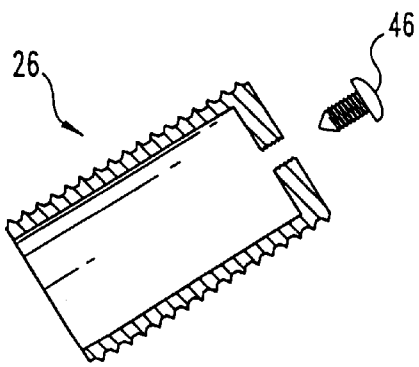
FIG. 3C is a sectional view illustrating a coupling member incorporating the present invention.
Figure 3D:
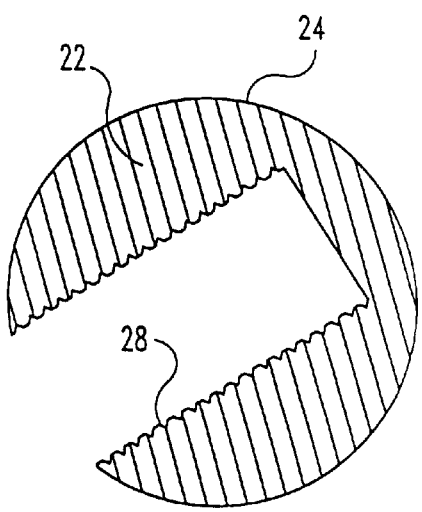
FIG. 3D is a sectional view illustrating a ball member incorporating the present invention.

FIGS. 1 and 2 show a modular hip implant 20 including a femoral ball member 22 having an outer surface 24 adapted to cooperate with an acetabular socket (not shown) or a prosthetic acetabular cup (not shown) as is known in the art. Coupling member 26 forms a tubular threaded insert which is threadingly received in threaded bore 28 of ball member 22. A spring mechanism 30 includes a spring element 32, shown in FIGS. 1 and 2 as a coiled spring having connectors 34 and 36 at opposite ends thereof. Connector 34 is received in a threaded opening 38 formed in femoral neck 40 of femoral stem 42. Connector 36 abuts against cap 44 of coupling member 26 and is secured thereto by means of a screw 46 received through threaded aperture 48 in cap 44 and threaded aperture 50 formed in connector 36.

Femoral stem 42 includes a shank 52 adapted to be inserted into a medullary cavity 54 (FIG. 2) of a patient by means of bone cement or other fixation means known in the art. Femoral stem 42 includes a circular hole 56 adapted for a medical instrument to be hooked thereto to remove the prosthesis should such become necessary during a surgical procedure. Triangular shaped fenestration 58 is provided to allow bone and scar tissue to grow therein and thereby prevent loosening or rotation of femoral stem 42. More than one fenestration can be provided, as is known in the art. Square shaped notch 60 is provided to accommodate an impactor or other suitable surgical instrument for implanting shank 52 into cavity 54. Femoral stem 42 includes a flange 62 that abuts femur bone portion 64 (FIG. 2) and prevents shank 52 from migrating downward into cavity 54 of femur 55.

Figure 4A:
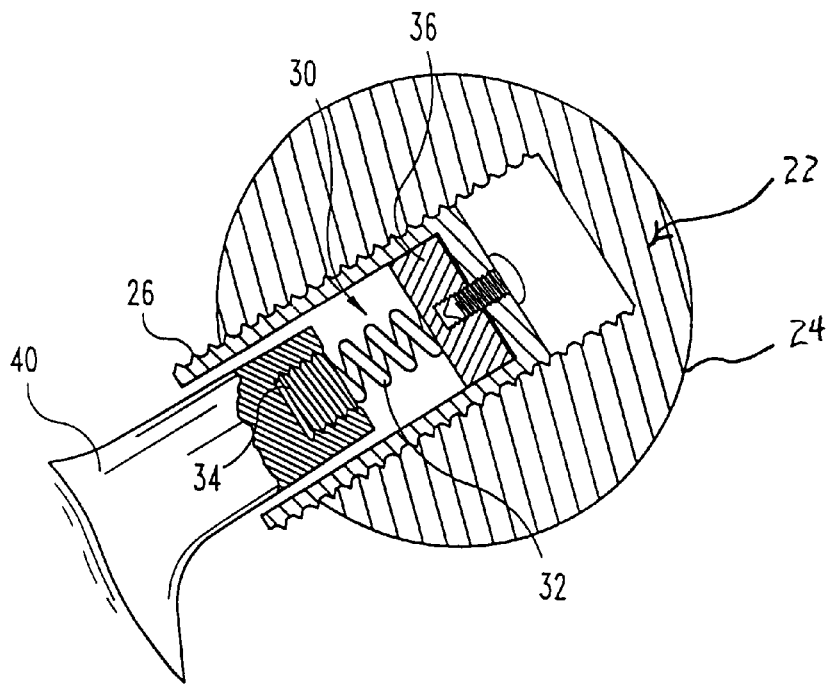
FIG. 4A is a sectional view illustrating the femoral neck extending from the ball member a first distance.
Figure 4B:
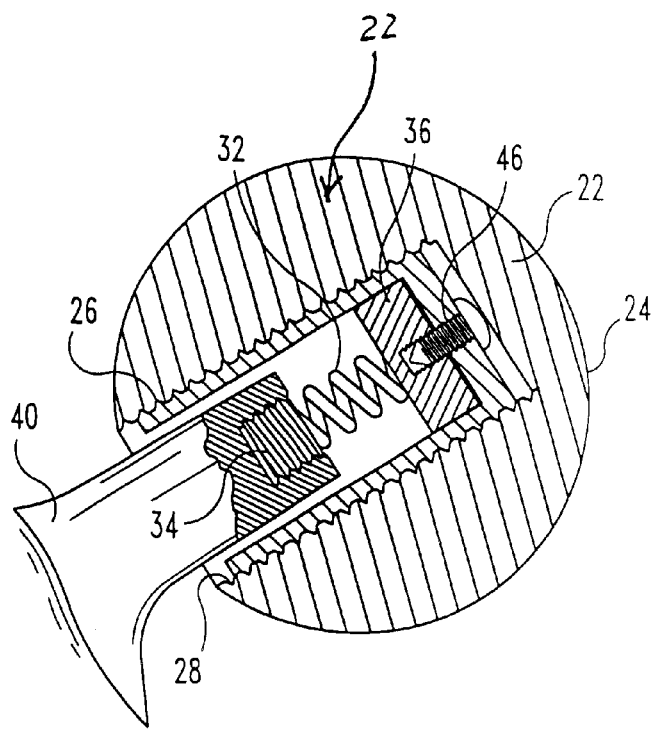
FIG. 4B is a sectional view illustrating the femoral neck of FIG. 4A extending from the ball member a second distance less than the first distance.

With reference to FIGS. 1–4, spring mechanism 30 includes a threaded connector 34, shown in FIGS. 4A and 4B as a threaded plug fixed to an end of spring element 32. The end of spring element 32 can be welded to or embedded within plug connector 34. The other end of spring element 32 can also be welded to or embedded within disk-shaped connector 36. Connector 34 is threadingly received into threaded opening 38 and, at the other end of spring mechanism 30, disk-shaped connector 36 is secured to cap 44 by means of screw 46.

It can be appreciated that the connection of neck 40 to coupling member 26 and thus to ball member 22 is through spring mechanism 30, which is disposed intermediate ball member 22 and neck 40. Similarly, the connection of spring mechanism 30 to ball member 22 is through coupling member 26. It can be also be appreciated that spring mechanism 30 is removable from coupling member 26 and thus from modular hip implant 20. Thus, hip implant 20 provides the flexibility of accepting a spring mechanism having different spring constants, or stiffnesses, if desired. Such may be desirable depending on the age, weight and activity level of the patient.

The spring mechanism is designed to absorb shock and vibrations produced by daily activities such as walking, running, exercising, and even simple load-bearing activities such as sitting and standing. Because the spring mechanism absorbs some of the shock and vibrations imparted to the implant, it is less likely that such shock and compressive stresses will cause the implant to loosen or fracture over a period of time. Further, because the stiffness of the spring can be pre-selected, its cushioning effect can be adjusted for an individual patient. For example, a spring element 32 that is too stiff will frustrate the load-sharing purpose of the implant. On the other hand, if the spring element is not stiff enough, the implant will experience too much movement. With the present invention, the stiffness of the spring can be selected to provide the appropriate cushioning effect.

As shown in FIG. 1, coupling member 26 is formed as a substantially hollow, tubular insert having an open distal end to receive neck 40. Neck 40 has an outer surface 66 that corresponds to a substantially smooth inner surface 68 of coupling member 26 such that neck 40 slidably engages coupling member 22. Various low-friction, bio-compatible coatings can be applied to the two surfaces 66, 68. Preferably, the two mating surfaces are cylindrical, although other complementary shapes are contemplated. At least half and preferably two-thirds of neck 40 should be housed within coupling member 26 to adequately secure neck 40 to coupling member 26. The spring mechanism and the sliding engagement between surfaces 66 and 68 combine to provide a cushioning movement between neck 40 and ball member 22.

With reference to FIGS. 4A and 4B, one of the features of modular hip implant 20 is that the extent to which neck 40 extends from ball member 22 is an adjustable parameter, depending on characteristics of the individual patient. That is, coupling member 22, to which neck 40 of stem 42 is removably attached, can be screwed into bore 28 to a depth that corresponds to the desired extension distance of neck 40 from ball member 22. Thus, the present invention avoids the necessity of interchangeable sleeves of different sizes to produce different length necks. Instead, a continuous range of neck lengths are made possible with a single coupling member 26. For example, the configuration shown in FIG. 4A can accommodate a patient needing a larger femoral neck length whereas the configuration in FIG. 4B may accommodate a person needing a shorter femoral neck length. Further, it is possible with the present invention to adjust the femoral neck length at the time of surgery, which might be desirable, for example, when preoperative data used to establish femoral neck length are inaccurate.

Figure 5A:
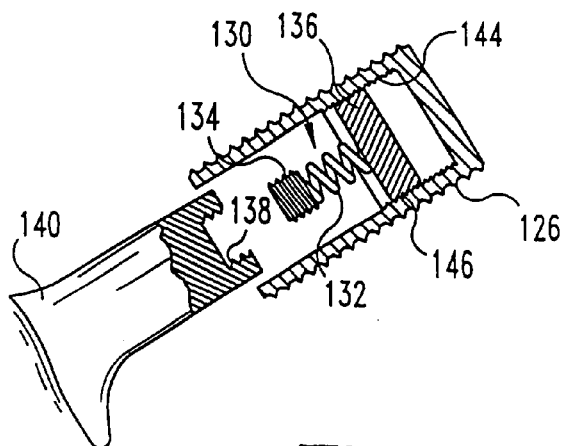
FIGS. 5A–5E are sectional views illustrating alternate embodiments of the spring mechanism in accordance with the present invention.

Alternate embodiments of the spring mechanisms are possible. For example, as shown in FIG. 5A, spring mechanism 130 can include spring element 132 having threaded connectors 134 and 136 at opposite ends thereof. Coupling member 126 has a portion of its interior formed with a thread 144 which threadingly engages threads 146 formed on connector 136. This arrangement provides an additional means to adjust the length that neck 140 extends from the ball member because the relative position of connector 136 can be varied by the extent to which it is screwed into coupling member 126.

Figure 5B:
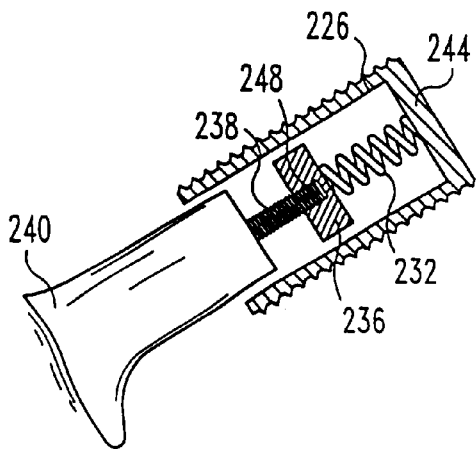

As shown in FIG. 5B, neck 240 can be formed with a threaded fastener 238 which screws into a threaded aperture 248 formed in connector 236. Spring element 232 is fixed to connector 236 at one end and is fixed to cap 244 of coupling member 226 at its other end.

Figure 5C:
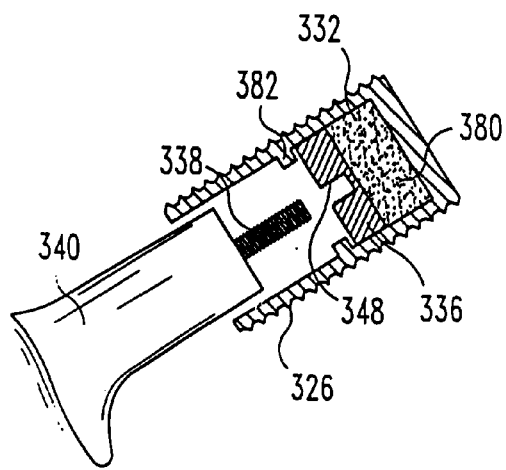

As shown in FIG. 5C, neck 340 can be formed with a threaded fastener 338 which screws into a threaded aperture 348 disposed in connector 336. Spring element 332 can be formed of a compressible and elastic material such as silicone, closed gel foam, rubber or the like. Sufficient elastic material is placed in the cavity 380 such that connector 336 is biased against stop 382 which can be formed as an annular ridge or as a crimped portion on the inside of coupling member 326 as shown.

Figure 5D:
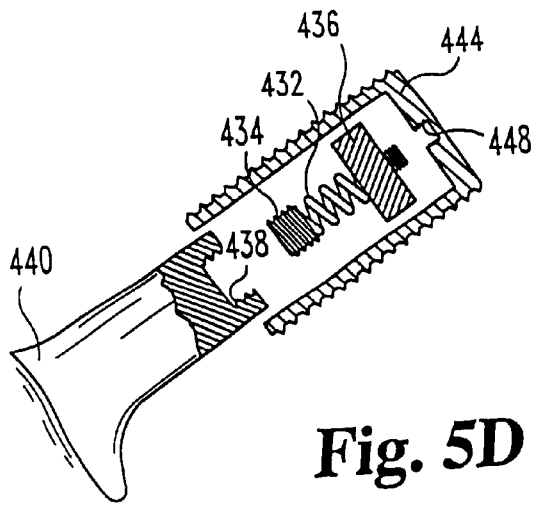

FIG. 5D illustrates an embodiment similar to the embodiment described with reference to FIGS. 1–4, except that cap 444 of coupling member is formed with an internally threaded bore 448 that receives threaded fastener 446 extending from connector 436. On the other end of spring element 432 is attached a threaded connector 434 that screws into bore 438 formed in neck 440.

Figure 5E:
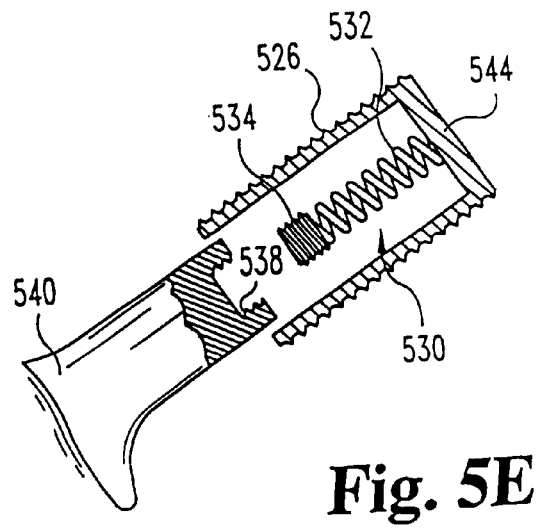

FIG. 5E illustrates an embodiment wherein spring mechanism 530 is fixed within coupling member 526. An end of spring element 532 is fixed to cap 544 of coupling member 526. As with other embodiments described above, threaded connector 534 is received in bore 538 formed in neck 540.

Figure 5F:
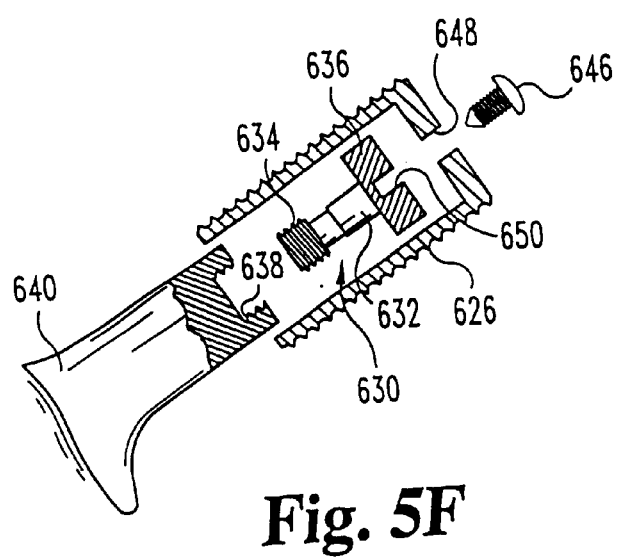

FIG. 5F illustrates an embodiment wherein spring mechanism 630 includes a piston-cylinder spring element 632 connected at one end to connector 634 and connected at its other end to connector 636. Spring mechanism 630 is detachably connected to coupling member 626 by means of screw 646 that passes through aperture 648 and is threadingly received in threaded opening 650. Connector 634 is received in threaded bore 638 formed in neck 640.

The advantages of the modular features of the present invention can be better understood with reference to a description of custom fitting a modular hip implant to an individual patient. Ball member 22 can be selecting from a plurality of different size ball members, depending upon the size of the acetabular socket into which the ball member is to be inserted. The acetabular socket can be the patient's acetabulum or a prosthetic acetabular cup that is fixed into the patient's pelvic bone. The femoral stem component 42 is selected from a plurality of different size femoral stems. The femoral stems may vary, among other parameters, by length and/or diameter of the femoral shank, angle of femoral neck with respect to the femoral shank, and length and/or diameter of femoral neck.

A spring mechanism 30 is selected for the individual patient and installed into the coupling member 26. The stiffness of spring element 32 can be chosen based upon various patient factors, such as weight and activity level. With reference to FIG. 1, connector 36 is placed against cap 44 such that apertures 48 and 50 are aligned. Screw 46 is then threadingly advanced through the apertures, thereby securing spring mechanism 30 to coupling member 26. Femoral stem 42 is connected to spring mechanism 30 and thus coupling member 26 by aligning connector 34 with bore 38 and turning coupling member 26 such that connector 34 is screwed into bore 38.

After coupling member 26 is secured to stem 42 as just described, coupling member 26 is inserted into bore 28 of the selected ball member to a specific depth. Based upon patient data such as computer assisted tomography images (CAT scans), magnetic resonance imaging (MRI) and the like, the appropriate length of the patient's femoral neck can be determined preoperatively and then correlated to determine the corresponding depth to which coupling member 26 should be inserted into ball member 22. Advantageously, if the length of the neck as determined preoperatively does not exactly match the actual length needed as determined during surgery, the length of the neck can be adjusted during surgery by turning the ball member 22 relative to coupling member 26.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A modular hip prosthesis comprising:

a ball member having an outer surface adapted to cooperate with an acetabular socket, said ball member having a first bore;

a femoral stem having a shank adapted to be inserted and secured into a medullary cavity of a femur bone, said femoral stem having a neck member at a proximal end, said neck member having a second bore;

a coupling member removably attached into said first bore and slidably engagable over the neck member of said femoral stem; and an intermediate spring mechanism having a first end and second end, the first end is attached to the coupling member and the second end is attached to the second bore of said neck member providing a cushioning movement between said acetabular socket and said ball member.

2. The modular hip prosthesis of claim 1, further comprising:

the coupling member housing said spring mechanism, the connection of said ball member to said spring mechanism being through said coupling member, said coupling member received in said bore to an adjustable depth, adjustment of said depth causing corresponding adjustment of the distance said neck extends from said ball member.

3. The modular hip prosthesis of claim 2, wherein said bore and said coupling member comprise corresponding threads, said coupling member being threadingly received in said bore.

4. The modular hip prosthesis of claim 2, wherein said spring mechanism includes a first connector at the first end thereof connecting said neck to said spring mechanism.

5. The modular hip prosthesis of claim 4, wherein said first connector and said neck include complementary threads, said first connector threadingly connected to said neck.

6. The modular hip prosthesis of claim 4, wherein said spring mechanism includes a second connector at the second end thereof connecting said spring mechanism to said coupling member.

7. A method of custom-fitting a modular hip prosthesis comprising the following steps:

selecting a ball member from a plurality of different size ball members, said ball member having an outer surface and a first bore;

selecting a femoral component from a plurality of different size femoral components, said femoral stem having a neck member at a proximal end and said neck member having a second bore;

attaching the neck of the selected femoral component to a coupling member, said coupling member is removably attached into said first bore and slidably engages over the neck member of said femoral stem;

determining a depth corresponding to an individual patient that the coupling member is to be inserted into the selected ball member; and installing the coupling member into the ball member to the determined depth.

8. The method of claim 7, further comprising installing a spring mechanism into the prosthesis to allow cushioning movement of the neck of the selected femoral component relative to the ball member.

9. The method of claim 8, further comprising selecting the spring mechanism from a plurality of spring mechanisms having spring elements of different stiffnesses.

10. The method of claim 7, further comprising adjusting the depth intraoperatively.

* * * * *